United States Patent [19]

Buchalter

[11] 3,983,252
[45] Sept. 28, 1976

[54] STABLE DIALDEHYDE-CONTAINING DISINFECTANT COMPOSITIONS AND METHODS

[76] Inventor: Gilbert Buchalter, 555 Mount Prospect Ave., Newark, N.J.

[22] Filed: Mar. 18, 1975

[21] Appl. No.: 559,513

Related U.S. Application Data

[63] Continuation of Ser. No. 410,044, Oct. 26, 1973, abandoned, which is a continuation of Ser. No. 316,388, Dec. 18, 1972, abandoned.

[52] U.S. Cl. ............................... 424/333; 424/317; 424/365; 21/58;82 R
[51] Int. Cl.$^2$ .......................................... A61L 13/00
[58] Field of Search ............................ 424/317, 333

[56] References Cited
UNITED STATES PATENTS

| | | | |
|---|---|---|---|
| 3,016,328 | 1/1962 | Pepper et al. | 424/127 |
| 3,282,775 | 11/1966 | Stonehill | 424/263 |

OTHER PUBLICATIONS

Remington's Pharmaceutical Sciences, 13th Ed., p. 502, (1965).

Chemical Abstracts 49:7052a, (1955).

Chemical Abstracts 47:11600b, (1953).

Merck Index, — 8th Ed., p. 851, (1968).

Merck Index, — 8th Ed., p. 853, (1968).

*Primary Examiner*—Leonard Schenkman
*Attorney, Agent, or Firm*—Lerner, David, Littenberg & Samuel

[57] ABSTRACT

Disinfectant compositions are provided which contain a dialdehyde and an alkali metal salt of a hydrocarbon carboxylic acid in aqueous solution and, optionally, an alcohol and/or a diol and/or a triol, and are as potent as, but substantially more stable than, known dialdehyde-containing disinfectant compositions. A method for disinfecting medical and surgical supplies and household objects is also provided wherein the above disinfectant compositions are employed.

18 Claims, No Drawings

STABLE DIALDEHYDE-CONTAINING DISINFECTANT COMPOSITIONS AND METHODS

This is a continuation of application Ser. No. 410,044 filed Oct. 26, 1973, now abandoned, which is a continuation of application Ser. No. 316,388 filed Dec. 18, 1972, now abandoned.

BRIEF DESCRIPTION OF THE INVENTION

This invention relates to improved chemical disinfecting compositions comprising a dialdehyde and an alkali metal salt of a hydrocarbon carboxylic acid and, optionally, an alcohol, in aqueous solution and to methods for disinfecting with these compositions.

BACKGROUND OF THE INVENTION

Incidence of hospital-acquired infections has been increasing in recent years at an alarming rate causing great concern among the staffs of these institutions. Many disinfection and sterilization techniques have been employed in an attempt to alleviate this problem. Steam sterilization under pressure has been widely used. However, this method has proven to be impracticable in that it requires expensive equipment and skilled technicians and does not lend itself to the disinfection of objects such as hospital beds, walls, floors or delicate instruments which are sensitive to elevated temperatures.

It has long been the feeling among hospital and medical personnel that a chemical germicide capable of sterilizing materials difficult to sterilize by steam sterilization and stable over relatively long periods of time would be highly desirable. Such a germicide must not only be active against vegetative bacteria but also against fungi, viruses and spores and must have the ability to penetrate tissue and materials, be relatively non-toxic, retain its activity in the presence of organic materials, be non-reactive to rubber and plastics, reach hard-to-get-at places, disinfect quickly, be substantially odorless, be non-corrosive, be non-irritating, be relatively easy to apply, and be safe for use on delicate or sensitive instruments.

Considerable research effort has been expended in finding and developing such a chemical germicide which would provide quick and safe sterilization and substantially replace steam sterilization. Unfortunately all presently known germicidal compositions have been found unacceptable for various reasons. The phenols and formaldehyde compositions which were originally intended to replace steam sterilization have been used and have considerable bactericidal activity, but both have objectionable odors and considerable toxicity. Ethanol, isopropyl alcohol and the quaternary ammonium compounds have been used, and though less odorous and toxic, lack the activity of the phenols and formaldehyde compositions.

Saturated dialdehydes, such as aqueous solutions of glutaraldehyde, have been found to possess surprisingly good disinfectant properties. However, while commercially available glutaraldehyde solutions by themselves having a pH ranging from 2.7 to 3.7 exhibit microcidal properties, they are not sporicidally active.

Compositions comprising saturated dialdehydes with alkalinating agents, such as alkali metal carbonates, bicarbonates or hydroxides and certain secondary and tertiary amines, in solution having a pH ranging from 7.5 to 10 have also been used. Such compositions are more fully described in U.S. Pat. No. 3,016,328. Though such compositions are quite satisfactory as chemical sterilization agents, their stability and potency retention is severely limited thereby rendering them commercially unfeasible except for specialized application. Furthermore, these disinfectant compositions are prepared in solution form preferably containing from 50 to 80% lower alkanol, such as methanol; use of such large amounts of alcohol could have a deleterious solvent effect on equipment.

U.S. Pat. No. 3,282,775 discloses chemical sterilization compositions comprising a saturated dialdehyde containing from 2 to 6 carbon atoms and a cationic surface active agent which may be used in either aqueous or alcoholic solutions. These compositions, as in the case of other prior art disinfectants, rapidly lose their potency once they have been formulated for sterilization use.

It has been found that saturated dialdehydes such as glutaraldehyde can be stored as an acidic aqueous solution (pH 2.5-4.5) at room temperature for 6 to 12 months without significant degradation of the material. However, as indicated hereinbefore, in acidic solution, glutaraldehyde is not sporicidally active. Moreover, near neutral or basic solutions of glutaraldehyde (which are sporicidally active) rapidly lose their potency primarily due to polymerization of the product. Further, elevated temperatures induce polymerization.

Until now the problem of maintaining potency of approximately neutral or basic solutions of glutaraldehyde over long periods of time has remained virtually unresolved. Rather than resolving this problem by developing a neutral or basic glutaraldehyde-containing formulation stable over substantial periods of time, the problem has been sidetracked or avoided by maintaining glutaraldehyde solution as an acidic solution until just prior to use when an alkaline material such as an alkali metal carbonate or certain amines would be added to the acidic solution thereby making it basic. Unfortunately, even this rather "indirect" approach to resolve the stability problem of the basic formulation has rather serious limitations in that the basic formulations apparently lose enough of their potency, due to chemical change, after only 2 to 3 weeks render them virtually ineffective as disinfectants.

It has now been found that stability and potency of saturated dialdehyde based disinfectants can be maintained over relatively long periods of time, substantially longer than prior at compositions, by incorporating in the disinfectant containing saturated dialdehyde, an alkali metal salt of a hydrocarbon carboxylic acid. The alkali metal salt not only acts as a buffer to stabilize pH of solutions of the dialdehyde to within the range of from about 6 to about 8, thereby enhancing disinfectant activity of the dialdehyde, but also inhibits polymerization of the dialdehyde, thereby increasing its stability and shelf-life and maintaining its potency against vegetative bacteria, fungi, viruses and spores over substantially longer periods than was possible with prior art neutral or basic solutions of dialdehyde. Furthermore, it has been found that stability and retention of potency of the dialdehyde is further enhanced by employing with the dialdehyde and alkali metal salt of a hydrocarbon carboxylic acid, an alcohol, diol and/or triol.

In fact, the combination of the alkali metal salt of the hydrocarbon carboxylic acid and the alcohol, diol and/or triol has been found to exhibit synergistic properties in enhancing stability and potency retention properties of basic or approximately neutral dialdehyde-containing formulations.

DETAILED DESCRIPTION OF THE INVENTION

Thus, in accordance with the present invention, there is provided a liquid disinfecting composition, which retains its potency and is substantially more stable than hitherto known dialdehyde-based disinfectants, comprising a saturated dialdehyde and an alkali metal salt of a hydrocarbon carboxylic acid.

In a preferred embodiment of the invention, the dialdehyde and alkali metal salt are employed in combination with an alcohol, diol and/or triol as described hereinafter.

Furthermore, there is provided a synergistic combination for enhancing the stability and potency retention properties of basic or approximately neutral dialdehyde formulations, comprising an alkali metal salt of a hydrocarbon carboxylic acid in combination with an alcohol, diol and/or triol.

As will be seen hereinafter, surprisingly, it has been found that the combination of the above alkali metal salt and alcohol, diol and/or triol is far superior to the alkali metal salt alone in imparting to the enhancing the stability of and therefore the potency retention properties of basic or approximately neutral dialdehyde formulations. Use of the alcohol, diol and/or triol alone with commercially available glutaraldehyde solution (pH 2.7 to 3.7) forms a solution of acidic pH which may have good stability but is inferior as a disinfectant. It has been found that the combination of the invention is substantially superior to either component taken alone, or the additive effects, thereof, in forming high potency disinfectants and enhancing stability of approximately neutral or basic saturated dialdehyde containing disinfectants.

In addition, a method for disinfecting medical and surgical supplies and instruments and household objects is provided wherein such objects are treated with a disinfecting composition comprising a saturated dialdehyde and an alkali metal salt of a hydrocarbon carboxylic acid and optionally, an alcohol, diol and/or triol.

The saturated dialdehydes which may be employed in the novel compositions of this invention are those containing from 2 to 6 carbon atoms. More specifically, these compounds include malonaldehyde, succinaldehyde, oxaldehyde (glyoxal), adipaldehyde and preferably, glutaraldehyde. Further, the dialdehyde may be in its pure form, acid form or in the form of an adduct, such as an alkali metal bisulfite adduct, i.e., glutaraldehyde bisulfite, or in other forms well known in the art.

The quantity of saturated dialdehyde which may be used in the claimed compositions may vary from about 0.1% to 3% depending upon which particular dialdehyde is selected. Moreover, one may safely depart from this concentration without seriously detracting from its effectiveness. For example, if desired, the final concentration of dialdehyde may be increased up to as much as 10% or decreased as low as 0.05%. However, amounts in excess of 2% are unnecessary and wasteful. In actual practice, a range of from 0.1% to about 2% is preferred.

The alkali metal salt of a hydrocarbon carboxylic acid can be employed in an amount within the range of from about 0.1 to about 2% by weight and preferably from about 0.1 to about 1% by weight and more preferably from about 0.3 to about 0.9% by weight of the total formulation. Examples of such salts which may be employed herein includes sodium, potassium, lithuim or cesium salts, with sodium or potassium salts being preferred. These alkali metal salts may be salts of hydrocarbon carboxylic acids containing from two to 25 carbon atoms and include a wide variety of acids such as substituted or unsubstituted alkanoic acids, alkenoic acids or aromatic acids, containing one, two or three carboxyl groups. These acids may contain substituents such as halogen, for example chloro; aromatic, for example phenyl or alkylphenyl; phenylalkyl; alkyl containing one to four carbons; alkenyl containing three to five carbons; and the like. Examples of suitable alkali metal salts which may be employed herein include sodium acetate, sodium propionate, sodium isopropionate, sodium butyrate, sodium isobutyrate, sodium pentanoate, sodium caproate, sodium caprylate, sodium caprate, sodium laurate, sodium myristate, sodium palmitate, sodium stearate, sodium benzoate, sodium phenylacetate, sodium trichloroacetate, sodium lactate, sodium malonate, sodium tartarate, sodium fumarate, sodium maleate, sodium acid maleate, sodium succinate, sodium citrate, sodium glutamate, sodium gluconate, sodium phthalate, sodium mandelate,, sodium cinnamate, sodium oleate, sodium oxalate, sodium pamoate, sodium ascorbate as well as the corresponding lithium and cesium salts. Preferred are sodium acetate, potassium acetate, sodium citrate and potassium citrate.

It has been found that where alkali metal carbonates, bicarbonates or hydroxides are employed in equivalent amounts to and in place of the alkali metal salt of the hydrocarbon carboxylic acid, with or without alcohol, the stability and potency retention of the final composition is substantially reduced.

The alkali metal salt is normally employed in a molar ratio to the dialdehyde of within the range of from about 0.05:1 to about 2:1 and preferably from about 0.1:1 to about 1:1 and optimally about 0.1:1 to ensure a pH of the final composition of the invention (in aqueous solution) of within the range of from about 6 to about 8 and preferably from about 6.5 to about 7.4.

Alcohols which may be employed herein include lower alkanols containing up to and including about seven carbons such as methanol, ethanol, propanol, isopropanol, butanol, pentanol, hexanol and heptanol. In addition, alkanediols containing from two to four carbons, such as ethylene glycol, propylene glycol, butylene glycol and like, as well as alkanetriols such as glycerol, may be employed.

The alcohol diol and/or triol is employed in an amount to provide a final concentration in the compositions of the invention of within the range of from about 0.5 to about 20% and preferably from about 1 to about 10.

In forming the synergistic combination of the invention, the alkali metal salt of the hydrocarbon carboxylic acid and the alcohol, diol and/or triol are employed in a weight ratio to each other of within the range of from about 0.1:1 to about 3:1 and preferably from about 0.2:1 to about 1:1 and optimally about 0.35:1.

Examples of synergistic combinations in accordance with the present invention include any of the alkali metal salts of hydrocarbon carboxylic acids taken together with any of the alcohols mentioned herein and preferably include, but are not limited to, sodium citrate-propylene glycol, sodium citrate-methyl alcohol, sodium acetate-propylene glycol, sodium acetate-methyl alcohol, potassium citrate-ethyl alcohol and potassium acetate-isopropyl alcohol.

Prior to using, the compositions of the invention are diluted with sufficient water or water-alcohol mixture to form aqueous or aqueous alcoholic solutions having a pH within the range of from about 6 to about 8, a dialdehyde concentration within the rage of from about 0.05 to about 10%, an alkali metal salt of a hydrocarbon carboxylic acid concentration to buffer to the above-desired pH and, where employed, an alcohol concentration within the range of from about 1 to about 20%, as indicated above.

Preferred compositions of the present invention comprise glutaraldehyde (about 2% by weight), sodium acetate or sodium citrate (about 0.7% by weight or less) in aqueous solution having a pH of about 7 and optionally containing propylene glycol or methanol (1 to 10 by weight).

The alcoholic and aqueous solutions of the dialdehyde, alkali metal salt and, optionally, an alcohol, diol and/or triol generally have a neutral or slightly basic pH which may be readily changed to a more alkaline pH, for example, up to about 11, by the addition of minor amounts of alkalinating agents or buffering agents such as the alkali metal carbonates, bicarbonates, phosphates, borates or certain amines, for example, sodium bicarbonate, potassium bicarbonate, sodium carbonate, diethylaminoethanol, dibutylamine, and the like. The excellent activity of the compositions of the present invention over the wide pH range makes them suitable for use in all types of environments and with most types of materials; furthermore, the wide pH range allows the solutions to be stored for long periods of time without detracting from their sporicidal activity.

The choice of aqueous, alcoholic, or aqueous alcoholic solutions will depend not only on the novel compositions used but also on the material to be sterilized. For instance, it is known that lower alkanols have a deleterious effect on materials such as rubber, certain plastics, lenses and on cements used in the optical field. When articles of this type are exposed to alcoholic solutions, particularly on a repetitive basis over protracted periods of time, the instruments and appliances lose their original characteristics because of corrosion, pitting, delamination or other detrimental effects, resulting in a short lifetime of usefulness. Further, if the materials to be sterilized have not been thoroughly cleansed, possible protein precipitation may occur with attendant danger of spore-encapsulation. These different effects can be eliminated by omitting deleterious alcohols from the inventive compositions and by control of the pH range of the sterilizing solution.

Other substances may be added to the novel compositions of the present invention provided they have no detrimental effect on the sporicidal activity of the compositions. Examples of such substances would be coloring materials, pH indicators, buffers, anti-corrosion agents, dyes, and the like.

The compositions of the invention may be formulated as a two componeent system, one component comprising an aqueous dialdehyde solution with or without alcohol and the other component comprising a powdered activator; namely, the alkali metal salt, with or without the alcohol, which is mixed with the solution as required for maximum germicidal activity and stability and potency retention. The dialdehyde component may also be in the form of a solid prepared by spray-drying a dialdehyde such as glutaraldehyde, in the form of an aqueous solution, in the presence of an inorganic sulfur acid salt. The resultant product, a solid, freeflowing powder, is the corresponding dialdehyde monosulfur acid salt which can be readily admixed with the alkali metal salt with or without the alcohol. The dual combination, if kept free of moisture will remain stable indefinitely, may be used to prepare extemporaneously a sporicidal solution by simple addition to the required volume of water or aqueousalcohol. Howeer, it is to be understood that the aqueous dialdehyde-alkali metal salt solution or aqueous-alcoholic dialdehyde-alkali metal salt solution has excellent stability and potency retention even when formulated as a single system.

Furthermore, the compositions of the invention may be formulated as concentrated solutions with water and/or alcohol added prior to usage.

The uses to which the novel compositions may be applied particularly because of their non-corrosive character, are many and varied. In the surgical and medical fields, various types of instruments and appliances may be safely sterilized by immersion for a period of about 2 to 12 hours at room temperature. As examples of objects suitable for chemical sterilization according to this invention may be given: catheters; clamps; foreceps; needles; syringes; scissors; scalpels; thermometers; and eye, ear nose and throat instruments. In home and industry, the noval compositions may be used in a similar manner to sterilize dishes, eating utensils, and enamelware as well as for disinfection of walls, floors and beds, the latter being accomplished by washing the objects with compositions of the invention.

The disinfectant compositions even when in activated form, that is having a neutral or basic pH, retains its potency for more than 4 months, and in many instances for more than 12 months, as compared to prior art compositions which lose their potency after 2 to 3 weeks. Furthermore, the inventive compositions even at relatively low pH's, for example, less than 7.4 when used against a wide spectrum of bacteria produce a total kill in 5 minutes or less, whereas prior art disinfectants requiring substantially higher pH's, such as 8 to 9.5 (U.S. Pat. No. 3,016,328) thus making the formulations substantially more caustic and dangerous to handle, require 10 minutes or more to disinfect against vegetative pathogens and require 10 hours for sterilization. In addition, such compositions of the invention produce a total spore kill in 2 to 4 hours, whereas presently available commercial disinfectant-sporicide product requires from 8 to 24 hours for total spore kill.

It has also been found that the stability of aqueous solutions of glutaraldehyde in acidic, basic or neutral form can be enhanced by adding to such glutaraldehyde solutions an alcohol, diol and/or triol as described hereinbefore. Such alcohol, diol and/or triol can be added in an amount ranging from about 0.25 to about 50% by weight of the composition. Such a stabilized composition by itself or in combination with any of the alkali metal salts of a hydrocarbon carboxylic acid can be employed as a disinfectant as described hereinbefore.

The compositions of the invention in combination with conventional preservatives, such as methyl p-hydroxy benzoate, benzoic acid and/or phenylmercuric acetate, are also useful in toiletry preparations.

The compositions of the invention can be included in toothpaste, dental creams or mouthwash. Further, such compositions can be added to conventional dry cleaning solvents to provide formulations which offer the advantage of simultaneously disinfecting and cleaning the textile without troublesome odor and do not require subsequent treatment such as a neutralization step of the garment.

The compositions of the invention may also find application in leather tanning, tissue fixation for electron microscopy, protein reactions and embalming fluids.

The following Examples further illustrate the invention. They are given primarily for the purposes of illustration and should not be construed as limiting the invention to the details given.

EXAMPLE 1

An activated and stabilized solution of glutaraldehyde in accordance with the invention is prepared by forming a soution of glutaraldehyde (50% aqueous solution) 40 cc, and mixing the glutaraldehyde solution with a solution of stabilizer comprising

| Sodium citrate | 7 gm |
|---|---|
| Propylene glycol | 50 cc |
| Water Q. S. | 960 cc | so that the final volume is about 25 times the volume of glutaraldehyde solution used.

The resulting formulation has a pH of about 6.8 and is useful for sterilization of medical equipment, dishes, eating and cooking utensils, walls, floors, beds and the like and is stable for about 6 months without loss of substantial disinfectant potency.

EXAMPLE 2

In a manner similar to that described in Example 1, 50 cc of methyl alcohol is employed in place of propylene glycol to form a disinfectant composition having a pH of about 6.8 in accordance with the invention. The resulting formulation has stability and potency properties similar to the Example 1 formulation.

EXAMPLE 3

In a manner similar to that described in Example 1, 7 gm of sodium citrate, without propylene glycol or methyl alcohol, is employed to form a disinfectant composition having a pH of about 6.8 in accordance with the present invention.

The resulting formulation has excellent stability and retains its disinfectant potency for more than 2 months.

EXAMPLES 4 to 6

In order to demonstrate that the combination of the alkali metal salt of the hydrocarbon carboxylic acid and the alcohol of the invention form a surprisingly excellent and, in fact, synergistic, combination for enhancing stability of glutaraldehyde formulations of approximately neutral or basic pH and retarding chemical changes therein, the following accelerated stability experiments were carried out.

Ten percent by weight solutions of glutaraldehyde in accordance with the invention were formed by diluting a commercially available 25% solution of glutaraldehyde having a pH of about 3 with mixtures of sodium citrate, methyl alcohol and water, or sodium citrate, propylene glycol and water; the resultant mixture had a pH or 7 and was crystal clear and colorless in appearance. The resulting formulations were maintained at 100°F. and maintained thereat for 37 days during which time they were observed for color, clarity and presence of precipitate. The presence of any change from the original crystal clear and colorless liquids would indicate chemical change, probably polymerization, and thus loss of disinfectant potency.

As a control, sodium citrate alone was employed with 10% glutaraldehyde to form a solution of abut pH 7.

Furthermore, in order to show the long-term superiority in stability and thus potency retention of the formulations of the invention over formulations of U.S. Pat. No. 3,016,328, sodium bicarbonate alone and sodium bicarbonate with methyl alcohol were employed with 10% glutaraldehyde solution to form solutions of pH about 7, which were heated at 100°F for 37 days and observed.

The results obtained and appearance of the formulations are tabulated in the followig table.

| Example No. | Additive to 10% Glutaraldehyde Solution (20 cc) | Approximate pH of Final Formulation (20 cc) | Appearance after heating at 100° F. for 28 hours | Appearance after heating at 100° F. for 37 days |
|---|---|---|---|---|
| 4 | Sodium citrate 2½ Methyl alcohol 5% | 7 | Crystal clear and colorless | Light yellow No precipitate |
| 5 | Sodium citrate 2½ Propylene glycol 5% | 7 | Crystal clear and colorless | Yellow liquid Very slight precipitate |
| 6 | Sodium citrate 2½ | 7 | Moderately cloudy liquid | Yellow-amber liquid Light amber precipitate |
| Control A | Sodium bicarbonate | 7 | Moderately cloudy liquid | Dark amber liquid Dark amber precipitate |
| Control B | Sodium bicarbonate Methyl alcohol 5% | 7 | Yellow clear liquid | Medium amber liquid Medium amber precipitate |

The results shown in the above Table clearly illustrate that the sodium citrate when used in combination with the methyl alcohol (Example 4) and with the propylene glycol (Example 5) forms a synergistic combination for enhancing stability and imparting resistance to chemical change of glutaraldehyde solution. As can be seen, the combinations of Examples 4 and 5 imparted excellent stability to the glutaraldehyde solution after 28 hours and 37 days at 100°F., whereas the sodium citrate alone (Example 6) had some, although substantially less, stabilizing effect. Glutaraldehyde solutions containing methyl alcohol alone and propylene glycol alone were not tested inasmuch as commercially available solutions are acidic and not basic or neutral and, therefore, do not have severe stability problems. However, they require unduly prolonged periods, such as several weeks to be effective against spores and, therefore, are not useful disinfectants. The results obtained clearly show that the combination of the citrate and alcohol was substantially superior to the citrate alone in enhancing stability of and thereby potency retention of glutaraldehyde solutions. Accordingly, such a combination of citrate and alcohol is indeed a synergistic combination for this purpose.

Furthermore, the results clearly show that the formulations of the invention (Examples 4 to 6) are substantially and significantly more stable than the representative formulations of U.S. Pat. No. 3,016,328 (Controls A and B). Even the Example 6 formulation of the invention (sodium citrate alone) enhances stability and resistance to chemical change of the glutaraldehyde solution to a substantially greater degree than the sodium bicarbonate alone (Control A) and sodium bicarbonate and methyl alcohol (Control B) as evidenced by the fact that after 37 days at 100°F., the control A formulation changed from a crystal clear and colorless liquid to a dark amber liquid containing a dark amber precipitate and the Control B formulation changed from a crystal clear and colorless liquid to a medium amber liquid containing a medium amber precipitate. The Example 6 formulation changed from a crystal clear and colorless liquid after 37 days at 100°F. to a yellowamber liquid containing a light amber precipitate indicating that the Example 6 formulation had undergone substantially less chemical change than the Controls A and B formulations. Furthermore, the preferred formulations of the invention (Examples 4 and 5) were vastly superior in enhancing stability and resistance to chemical change of glutaraldehyde solution than were the Controls A and B formulations (U.S. Pat. No. 3,016,328). As seen after 28 hours at 100°F., the Examples 4 and 5 formulations of the invention were substantially resistant to chemical change (crystal clear and colorless) whereas, the Controls A and B formulations were moderately cloudy and yellow, respectively indicating chemical change after 37 days at 100°F., the Examples 4 and 5 formulations of the invention underwent only relatively slight chemical changes (Example 4 — light yellow liquid, Example 5 — yellow liquid, very slight precipitate), whereas the Controls A and B formulations underwent substantial chemical change (Control A — dark amber liquid, dark amber precipitate, Control B — medium amber liquid, medium amber precipitate). These results clearly show the vast superiority of the formulations of the invention in long range stability and to resistance to chemical change over the formulations of U.S. Pat. No. 3,016,328.

Other formulations of the invention having similar stability and resistance to chemical change are obtained by substituting any of the other alkali metal salts of hydrocarbon carboxylic acids and alcohols and dialdehydes set out hereinbefore for the sodium citrate, methyl alcohol, propylene glycol and glutaraldehyde employed in the Examples. Furthermore, all of the formulations of the invention are effective as disinfectants against vegetative bacteria, fungi, viruses and spores.

What is claimed is:

1. A disinfectant composition comprising a saturated dialdehyde containing from 2 to about 6 carbon atoms; an alkali metal salt of a carboxylic acid containing from 2 to 25 carbon atoms and selected from the group consisting of sodium, potassium or lithium salts of alkanoic acids, sodium, potassium, or lithium salts of alkenoic acids, and sodium, potassium or lithium salts of aromatic acids; and a member selected from the group consisting of lower alkanols containing up to and including 7 carbon atoms, alkanediols containing from 2 to 4 carbon atoms, glycerol and mixtures thereof, said alkali metal salt of a carboxylic acid being present in a weight ratio to said dialdehyde within the range of from about 0.05:1 to about 2:1, said lower alkanol, alkanediol or glycerol being present in a weight ratio to said alkali metal salt of a carboxylic acid within the range of from about 1:0.1 to about 1:3, said composition when dissolved in water providing a solution having a pH of within the range of from about 6 to about 7.4.

2. A composition in accordance with claim 1 wherein said dialdehyde is glutaraldehyde.

3. A composition in accordance with claim 2 wherein said alkali metal salt of a hydrocarbon carboxylic acid is sodium acetate or sodium citrate.

4. A composition in accordance with claim 3 wherein said lower alkanol is methanol and said alkanediol is propylene glycol.

5. A composition in accordance with claim 1 in aqueous solution, said lower alkanol, alkanediol or glycerol being present in a concentration of from 1 to about 20% of said aqueous solution.

6. A composition in accordance with claim 1 wherein said dialdehyde is oxaldehyde.

7. A composition in accordance with claim 1 including in addition a minor amount an alkalinating agent.

8. A composition in accordance with claim 1 in aqueous solution said solution having a pH within the range of from about 6 to about 7.4.

9. A method for disinfecting medical and surgical supplies, and instruments and household objects, which comprises applying to said objects an effective amount of a composition as defined in claim 8.

10. A composition in accordance with claim 1 wherein said alkali metal salt is a salt of a carboxylic acid selected from the group consisting of acetic acid, propionic acid, isopropionic acid, butyric acid, isobutyric acid, pentanoic acid, caproic acid, caprylic acid, capric acid, lauric acid, myristic acid, palmitic acid, stearic acid, benzoic acid, phenylacetic acid, trichloroacetic acid, lactic acid, malonic acid, tartaric acid, fumaric acid, maleic acid, succinic acid, citric acid, glutamic acid, gluconic acid, phthalic acid, mandelic acid, cinnamic acid, oleic acid, oxalic acid, pamoic acid and ascorbic acid.

11. A composition as defined in claim 10 wherein said alkanediol comprises propylene glycol.

12. A disinfectant composition comprising glutaraldehyde, an alkali metal salt of a hydrocarbon carboxylic selected from the group consisting of sodium citrate or potassium citrate and an alcohol selected from the group consisting of lower alkanols containing up to and including seven carbons or propylene glycol said alkali metal salt being present in a weight ratio to said glutaraldehyde within the range of from about 0.05:1 to about 2:1, said alcohol being present in a weight ratio to said alkali metal salt within the range of from about 1:0.1 to about 1:3, said composition when dissolved in water providing a solution having a pH within the range of from about 6 to about 7.4.

13. The disinfectant composition as defined in claim 12, in aqueous solution, comprising from about 0.05 to about 10% by weight glutaraldehyde, from about 0.1 to about 2% by weight of sodium citrate or potassium citrate, and from about 0.5 to about 20% by weight of a lower alkanol containing up to and including seven carbons or propylene glycol.

14. A method for disinfecting medical and surgical supplies, and instruments and household objects, which comprises applying to said objects an effective amount of a composition as defined in claim 13.

15. The composition as defined in claim 12 wherein said lower alkanol is methanol.

16. The composition as defined in claim 12 comprising glutaraldehyde, sodium citrate and methanol or propylene glycol.

17. A method for increasing the stability of aqueous solutions of glutaraldehyde in acidic, basic or neutral form, which comprises adding from about 0.5 to about 20% by weight of a lower alkanol containing up to and including seven carbons or propyleneglycol and from about 0.1 to about 2% by weight of soliumcitrate or potassium citrate to said aqueous solution of glutaraldehyde.

18. A method of increasing the stability of aqueous solutions of glutaraldehyde or oxaldehyde, which comprises adding from about 0.5 to about 20 percent by weight of a lower alkanol containing up to and including 7 carbon atoms, or propylene glycol or glycerol, and from about 0.1 to about 2 percent by weight of an alkali metal salt of a carboxylic acid selected from the group consisting of sodium, potassium or lithium salts of alkanoic acids, sodium, potassium or lithium salts of alkenoic acids, or sodium, potassium or lithium salts of aromatic acids, to said aqueous solution of glutaraldehyde or oxaldehyde.

* * * * *